US005571478A

United States Patent [19]
Bartman et al.

[11] Patent Number: 5,571,478
[45] Date of Patent: Nov. 5, 1996

[54] METHOD AND SYSTEM FOR DETERMINING THE DESTRUCTION AND REMOVAL EFFICIENCY OF A THERMAL COMBUSTION DEVICE

[75] Inventors: Candace D. Bartman, Lexington, S.C.; Erin M. Connolly; Michael K. Crocker, both of Morgan City, La.; James H. Renfroe, Jr., Houma, La.

[73] Assignee: Marine Shale Processors, Inc., Baton Rouge, La.

[21] Appl. No.: 95,482

[22] Filed: Jul. 23, 1993

Related U.S. Application Data

[63] Continuation-in-part of Ser. No. 24,370, Mar. 1, 1993, abandoned, and Ser. No. 984,271, Dec. 1, 1992, abandoned, which is a continuation of Ser. No. 601,299, Oct. 22, 1990, abandoned.

[51] Int. Cl.$^6$ ............................ G01N 31/12; G01N 21/84
[52] U.S. Cl. ............................. 422/94; 436/155; 73/1 G; 73/23.31; 73/863.23; 73/863.81
[58] Field of Search ................................ 73/23.2, 23.31, 73/863.11, 863.23, 863.81, 864.81, 1 R, 1 G; 364/500, 502, 498, 499, 571.01, 496; 395/904, 906, 912, 914; 422/94; 436/62, 147, 155

[56] References Cited

U.S. PATENT DOCUMENTS

| | | |
|---|---|---|
| 3,449,958 | 6/1969 | Bailey ................................. 73/864.73 |
| 3,718,434 | 2/1973 | Pierce . |
| 3,848,548 | 11/1974 | Bolejack, Jr. et al. . |
| 3,960,500 | 6/1976 | Ross et al. . |
| 4,073,619 | 2/1978 | Lawson . |
| 4,094,187 | 6/1978 | Navarre . |
| 4,188,190 | 2/1980 | Muraki et al. ........................ 422/94 X |
| 4,322,964 | 4/1982 | Melgaard et al. ........................ 73/1 G |
| 4,578,986 | 4/1986 | Navarre . |
| 4,795,614 | 1/1989 | Norem et al. ....................... 73/23.31 X |
| 4,856,352 | 8/1989 | Daum et al. . |
| 4,922,841 | 5/1990 | Kent . |
| 4,974,453 | 12/1990 | Hohorst . |
| 4,974,455 | 12/1990 | McGowan et al. . |
| 5,060,503 | 10/1991 | Spohn et al. .............................. 73/1 G |
| 5,133,267 | 7/1992 | Kent et al. . |
| 5,239,492 | 8/1993 | Hartwig et al. ...................... 364/571.01 |

FOREIGN PATENT DOCUMENTS 1 496 887   1/1978   United Kingdom ............. G01N 1/22

OTHER PUBLICATIONS

E. Timothy Oppelt, Incineration of Hazardous Waste, The International Journal of Air Pollution Control Waste Management (JAPCA) vol. 37, No. 5, May, 1987, 558–586.

Kun–chieh Lee, Research Areas for Improved Incineration System Performance, The International Journal of Air Pollution Control and Waste Management (JAPCA), vol. 38, No. 12, Dec. 1988, 1542–1550.

C. C. Lee, et al., Hazardous/Toxic Waste Incineration, Journal of the Air Pollution Control Assoc., vol. 36, No. 8, Aug. 1986, 922–931.

Edward B. Overton, Development of Real–Time Stack–Gas Analysis Methods, Journal of Hazardous Materials, 22 (1989) 187–194.

Anthony J. Bunicore, Experience With Air Pollution Control Equipment and Continuous Monitoring Instrumentation on Hazardous Waste Incinerators, Journal of Hazardous Materials, 22 (1989) 233–242.

R. A. Bartera et al., "Continous HC1 Air Indicator", Nasa Tech Briefs, vol. 1, No. 1, p. 69, 1976.

The Daily Review, Continuous Monitoring System Brings MSP Worldwide Acclaim, vol. 27, No. 115, Jun. 9, 1989.

C. A. Whitehurst et al., Montoring Emissions For a Hazardous Waste. Presented to the 5th International Conference on Hazardous Waste Management, Technology and Public Policy, Rome, Itx, Apr. 1989.

C. A. Whitehurst et al., Design of a Real–Time Stack Monitoring System for Speciated Compounds at a Hazardous Waste Recycling Facility. Presented at the International Incinerator Conference, Knoxville, Tennessee, May 4, 1989.

George Harlow et al., Design of a Continuous Emissions Monitoring System at a Manufacturing Facility Recycling Hazardous Waste. Presented to Hazardous Materials Control Research Institute, Great Lakes 90, Sep. 1990.

C. D. Bartman et al., A Mass Spectrometer–Based Continuous Emissions Monitoring System for Hazardous Waste Stack Gas Measurements. Presented at the Int'l Joint Power Generation Conference, Oct. 22, 1990.

R. McInnes et al., "Feasibility Study For Adapting Present Combustion Source Continuous Monitoring Systems To Hazardous Waste Incinerations" Industrial Environmental Research Lab., pp. 1–69, (Mar. 1984).

C. Bartman, "A Mass Spectrometer–Based Continuous Emissions Monitoring System For Acid–Gas Emissions And Dre Demonstration," Industrial, Municipal, and Medical Waste Incineration Diagnostics and Control, vol. 1717, pp. 20–33, (1993).

*Primary Examiner*—Robert J. Warden
*Assistant Examiner*—E. Leigh Dawson
*Attorney, Agent, or Firm*—Finnegan, Henderson, Farabow, Garrett & Dunner, L.L.P.

[57] ABSTRACT

Methods of assessing the destruction and removal efficiency (DRE) of a thermal combustion device having a gaseous effluent according to the formula $$DRE = 100 \times (W_{in} - W_{out})/W_{in}$$

where:

$W_{in}$ = mass feed rate of an organic compound into the device, and $W_{out}$ = the mass emission rate of the organic compound in the gaseous effluent. An apparatus for determining the destruction and removal efficiency of a thermal combustion device is also described. The methods and apparatus are capable of assessing the DRE in real time and are particularly useful in thermal combustion devices regulated by the U.S. Environmental Protection Agency that combust or burn hazardous materials containing organics.

24 Claims, 5 Drawing Sheets

METHOD AND SYSTEM FOR DETERMINING THE DESTRUCTION AND REMOVAL EFFICIENCY OF A THERMAL COMBUSTION DEVICE

CROSS-REFERENCE TO RELATED APPLICATIONS

The present application is a continuation-in-part of U.S. patent application Ser. No. 08/024,370 filed Mar. 1, 1993, now abandoned, and a continuation-in-part of U.S. patent application Ser. No. 07/984,271 filed Dec. 1, 1992, now abandoned, which is a continuation of U.S. patent application Ser. No. 07/601,299 filed Oct. 22, 1990, now abandoned.

BACKGROUND OF THE INVENTION

Controlling the emission of hazardous organic compounds and acid gases from thermal combustion devices is an increasingly important environmental and regulatory issue. Emission of hazardous organic compounds and acid gases can result from hazardous organic compounds present in the feedstocks and/or fuels combusted in thermal combustion devices. Alternatively, thermal combustion devices may operate in a manner causing the formation of hazardous organic compounds and acid gases as products of incomplete combustion.

Due to environmental problems associated with thermal combustion devices emitting hazardous organic compounds and acid gases, the U.S. Environmental Protection Agency regulates thermal combustion devices under the Resource Conservation and Recovery Act and the Clean Air Act. Examples of regulated thermal combustion devices are, but not limited to, boilers and industrial furnaces which use recyclable hazardous wastes as fuels and feedstocks, and hazardous waste incinerators which are used to destroy hazardous wastes. Operators of regulated thermal combustion devices are required to demonstrate that the device meets a Destruction and Removal Efficiency (DRE) of 99.99% for certain organic compounds fed into the device.

At the present time, measuring the DRE is an expensive and time-consuming process that is not, and generally cannot be, performed on a routine or ongoing basis. Generally, infrequent DRE measurements are performed to insure that a given thermal combustion device is actually operating at or above the required DRE.

There is a need, therefore, to develop a method and apparatus capable of monitoring toxic organic compounds, and their combustion products. As a part of a responsible environmental policy, it is also important for industrial operators to demonstrate to local communities that an emission source, such as a thermal combustion device, is routinely operating in compliance with and well within environmental guidelines.

Recently, there have been promulgated standards for the operation of thermal combustion devices, combusting hazardous waste materials and forming a gaseous effluent, requiring them to demonstrate the effective removal or destruction of organic compounds within the material combusted. As used here, a thermal combustion device is any device which uses controlled flame, infrared, plasma arc or other means to generate high temperature combustion of organic bearing materials and which generate gaseous effluent from the combustion process. Generally speaking, thermal combustion devices must demonstrate a destruction and removal efficiency (DRE) of 99.99 percent for one or more principal organic hazardous constituents (POHCs) in the material to be combusted. The POHCs are chosen based on the degree of difficulty of destruction or their "hard-to-burn" ranking. Examples of the POHCs which can be chosen for a DRE determination are listed in Appendix VIII (Hazardous Constituents) to 40 C.F.R. §261, which is incorporated herein by reference.

Exposure to high levels of certain organic compounds has been shown to result in a variety of acute and toxic effects in animals. These effects can include damage to liver and kidneys, as well as to the central nervous system and the cardiovascular system. Carcinogenic effects, at least in animals, have also been demonstrated from exposure to certain organic chemicals. Benzene, vinyl chloride, carbon tetrachloride, 1,2-dichloroethane, trichloroethylene, and tetrachloroethylene, are considered to be known or probable carcinogens in humans.

The percent destruction and removal efficiency (DRE) of a thermal combustion device for a given organic compound or POHC is defined by the following equation:

$$DRE = 100 \times (W_{in} - W_{out})/W_{in}$$

where:
$W_{in}$ = mass feed rate of an organic compound into the device; and
$W_{out}$ = the mass emission rate of the organic compound in the gaseous effluent.

Conventionally, the destruction and removal efficiency of a thermal combustion device is determined using a trial burn. In a trial burn, a known organic compound is fed into the thermal combustion device at a known rate with the material normally combusted in the device. This provides the mass feed rate, $W_{in}$. In the typical trial burn, the organic compound is fed into the thermal combustion device for at least two hours per test and each test is generally repeated three times.

After destruction, usually by combustion, in the thermal combustion device, the organic compounds present in the gaseous effluent within the stack are collected in a trap for a period of time, generally two hours, to concentrate the sample. A commonly used device is a volatile organic sample train (VOST) sampler equipped with a Tenax® trap. The trap is then sent to a laboratory where the organic compounds are desorbed and analyzed usually by gas chromatography and/or mass spectrometry techniques, to determine the mass emission rate, $W_{out}$. Having directly determined $W_{in}$ and $W_{out}$ in this manner, the DRE of the thermal combustion device for the organic compound of interest can then be calculated.

This type of direct DRE determination for a thermal combustion device suffers from several disadvantages. If a thermal combustion device is operating at 99.99 percent DRE, the concentration of an organic compound in the gaseous effluent is too low to permit its concentration to be determined from a single unconcentrated sample. Thus, the gaseous effluent sampled is concentrated to allow the organic compounds present in the effluent to be analyzed. The concentrated sample is then analyzed off-site. This does not allow for real time determination of the DRE of a thermal combustion device to ensure that it is operating within the appropriate environmental guidelines.

The cost of a trial burn is also a disadvantage. Generally, an outside crew is hired to perform the trial burn. Additionally, the cost of the known organic compound or POHC being used in the trial burn is not insignificant.

Another significant disadvantage is the time requirements of a trial burn. First, a typical trial burn requires two to three days to set up and perform the test. Secondly, there is often a significant time delay between when the trial burn is run and when the results are available to the operator.

Due to the disadvantages associated with a trial burn, these tests are typically performed only at intervals of three to five years. Consequently, there is no assurance that operation of the thermal combustion device between test intervals is consistent with the operation of the device during the trial burn or within the appropriate environmental guidelines.

Therefore, one object of the present invention is to provide an inexpensive method of determining the destruction and removal efficiency of a thermal combustion device without the necessity of using large amounts of material containing hazardous organic compounds.

A second object of the invention is to provide an indirect method for assessing the destruction and removal efficiency of a thermal combustion device.

A third object of the invention is to provide a method and apparatus for assessing the destruction and removal efficiency of a thermal combustion device in real time.

Other objects and advantages of the present invention will be apparent from the following specification or would be readily apparent to those skilled in the art to which this invention pertains.

SUMMARY OF THE INVENTION

To achieve these and other objects of the invention there is provided a method of assessing the destruction and removal efficiency (DRE) of a thermal combustion device having a gaseous effluent according to the formula $$DRE=100\times(W_{in}-W_{out})/W_{in}$$

where:

$W_{in}$=mass feed rate of an organic compound into the device, and $W_{out}$=the mass emission rate of the organic compound in the gaseous effluent.

According to the method, at least one known organic compound is fed into the thermal combustion device at a known rate to provide $W_{in}$. The organic compound is combusted to form a gaseous effluent and the gaseous effluent sampled at a first location. The concentration of the organic compound in the sampled effluent is measured. An expected $W_{out}$ is calculated for a desired DRE based on $W_{in}$. An amount of the organic compound is then injected into the gaseous effluent at a known rate less than or equal to the expected $W_{out}$ and sufficient to be detected. The organic compound is injected at a second location upstream from the first location and downstream from any means for removing the organic compound from the gaseous effluent. The gaseous effluent is sampled a second time at the first location; and the concentration of the organic compound measured in this sampled effluent.

To achieve the above objects there is also provided a system for assessing the destruction and removal efficiency of a thermal combustion device having a gaseous effluent. The system comprises means for introducing at least one known organic compound into the device and means for combusting that organic compound to form a gaseous effluent. The system also comprises an injector at a first location within the gaseous effluent downstream from any means for removing organic compounds from the gaseous effluent. The injector being disposed to inject an amount sufficient for detection of the organic compound at a known rate into the gaseous effluent. The system also comprises a sampler at a second location within the gaseous effluent, downstream from the injector. The sampler is disposed to extract samples of the gaseous effluent. There is at least one heated transfer line in flow communication with the sampler and an analyzing system in flow communication with the transfer line. The analyzing system is capable of measuring the concentration of the organic compound within the gaseous effluent.

In another embodiment accomplishing the above objects, there is provided a method of assessing the destruction and removal efficiency (DRE) of a thermal combustion device having a gaseous effluent according to the formula $$DRE=100\times(W_{in}-W_{out})/W_{in}$$

where:

$W_{in}$=mass feed rate of an organic compound into the device, and $W_{out}$=the mass emission rate of the organic compound in the gaseous effluent.

This method comprising the steps of: feeding at least one known organic compound into the thermal combustion device at a known rate to provide $W_{in}$; calculating an expected $W_{out}$ for a desired DRE based on $W_{in}$; combusting the organic compound to form a gaseous effluent; injecting an amount of the organic compound into the gaseous effluent at a known rate less than or equal to the expected $W_{out}$ and sufficient to be detected, the organic compound being injected at a first location downstream from any means for removing organic compounds from the gaseous effluent; sampling the gaseous effluent at a location downstream from the first location; and measuring the concentration of the organic compound in the sampled effluent.

A further embodiment of the invention is a method of assessing the destruction and removal efficiency (DRE) of a thermal combustion device having a gaseous effluent according to the formula $$DRE=100\times(W_{in}-W_{out})/W_{in}$$

where:

$W_{in}$=mass feed rate of an organic compound into the device, and $W_{out}$=the mass emission rate of the organic compound in the gaseous effluent.

The method of this embodiment comprises the steps of: feeding at least one known organic compound into the thermal combustion device at a known rate to provide $W_{in}$; combusting the organic compound to form a gaseous effluent; sampling the gaseous effluent at a first location; and measuring the concentration of the organic compound in the sampled effluent.

The present invention will be disclosed in terms of various preferred embodiments. Those embodiments are depicted in the following figures which form a part of the specification.

DESCRIPTION OF PREFERRED EMBODIMENTS

Figure 1:
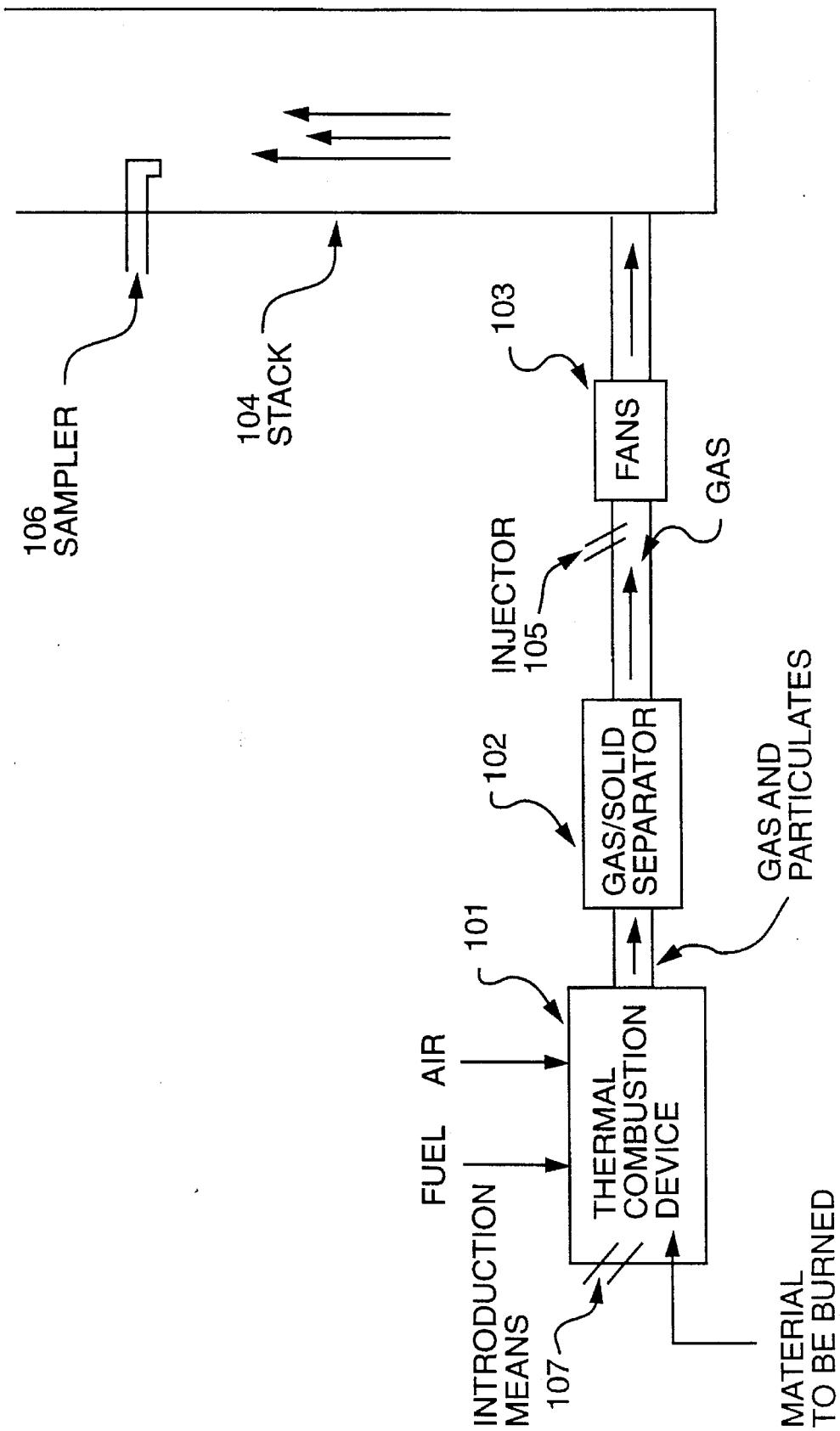
FIG. 1 is a schematic drawing of a thermal combustion device illustrating the preferred relationship of the injector and sampler.

The various embodiments described below are intended for use in thermal combustion devices which produce gaseous effluents in need of monitoring. FIG. 1 is a schematic of a thermal combustion device. The material to be combusted is introduced into the device (101) through an introduction means (107) along with fuel and air. An organic compound for a DRE determination can be introduced along with the material or separately. After combusting the material, gaseous effluent and noncombustible fine particulate matter leave the device and enter a gas/solid separator (102). The separator (102) can be one or more filters operating in series or in parallel. Where the gaseous effluent and fine particulate matter are introduced to the separator at temperatures between 350° and 400° F., conventional baghouse filters can be used. Having been separated from the fine particulate matter, the gaseous effluent is then passed into the atmosphere through a stack (104) by fans (103), preferably induced draft fans, located between the gas/solid separator (102) and the stack (104).

The present invention is particularly intended for use with thermal combustion devices which use recyclable hazardous wastes as feedstocks and fuels to manufacture products and thermal combustion devices which are used to dispose of hazardous waste, especially waste containing hazardous organic chemicals. Examples of such thermal combustion devices and their operation are described in U.S. Pat. Nos. 4,922,841, 4,986,197 and 5,133,267. These patents are incorporated herein by reference.

In a first embodiment, this invention relates to a system for determining the destruction and removal efficiency of a thermal combustion device. In this embodiment the overall system can be divided into four subsystems: the introduction and combustion subsystem, the injection subsystem, the sample extraction subsystem, and the detection subsystem. Each subsystem may be computer controlled to provide a fully automated system. Preferably, the system for determining the destruction and removal efficiency of a thermal combustion device is controlled by the computer system used to operate or monitor the thermal combustion device. In a particularly preferred embodiment, the sample extraction subsystem, and the detection subsystem are combined in a mass spectrometer-based continuous emissions monitoring system (CEMS). A CEMS is described in U.S. patent application Ser. No. 07/984,271 which is incorporated herein by reference.

The Introduction and Combustion Subsystem

In accordance with the invention there is provided means for introducing at least one known organic compound into a thermal combustion device and means for combusting that organic compound. As embodied herein the means for introducing the material is located upstream from the device and can be any means or opening normally used to introduce material to be combusted into a thermal combustion device.

Figure 3:
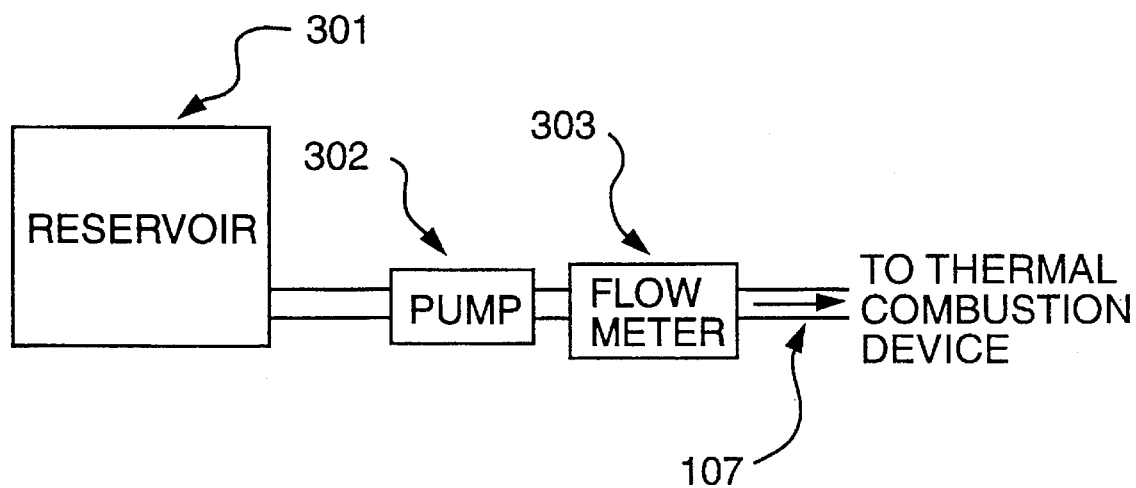
FIG. 3 is a schematic drawing of a preferred introduction subsystem.

FIG. 3 depicts a preferred embodiment of the introducing means according to the present invention. A reservoir (301), preferably a 500 gallon tank, capable of receiving an organic compound to be introduced into the thermal combustion device is in flow communication with a pump (302), preferably a diaphragm pump used to introduce the organic compound into the thermal combustion device. In the preferred embodiment, the diaphragm pump is a variable rate pump with a maximum pumping capacity of 2 gpm (7.6 L/min). The pump is in flow communication with a flow meter (303) to measure the rate of known organic compound introduced into the thermal combustion device. The flow meter is in flow communication with the introduction means (107), preferably a conduit, disposed to introduce the organic compound into the thermal combustion device. The flow meter is preferably of glass, Teflon™ and/or stainless steel construction.

The function of the introducing means is to introduce an amount of at least one known organic compound at a known rate to establish $W_{in}$ for the assessment of the thermal combustion device's DRE. The organic compound introduced can be introduced separately from (or together with) other material combusted in the normal operation of the thermal combustion device.

The organic compound can be any type of organic compound capable of being combusted or normally combusted in the thermal combustion device. Preferred organic compounds are those subject to environmental regulation and more preferred are hazardous organic compounds. Organic compounds specifically contemplated are those discussed above and in Appendix VIII to 40 C.F.R. §261. Advantageously, the present invention can be used to assess the DRE for more than one organic compound in the gaseous effluent simultaneously. As described below for the analyzing subsystem, a mass spectrometer is particularly preferred as the detector when assessing the DRE's of multiple organic compounds.

The known organic compound introduced into the thermal combustion device is combusted to form a gaseous effluent. As embodied here the introduction and combustion subsystem of the present invention comprises means for combusting the organic compound and other material normally introduced into the thermal combustion device. The combustion process can be accomplished in a single or multiple stages depending on the particular thermal combustion device. The present invention is not limited to any particular thermal combustion device, design or process. Where the material normally combusted contains hazardous waste, it is preferable to employ a rotary kiln, more preferably a counter current rotary kiln, as described in U.S. Pat. Nos. 4,922,841, 4,986,197 and 5,133,267, which are incorporated herein by reference.

After the material is combusted in the thermal combustion device, the gaseous effluent and any noncombustible fine particulate leave the thermal combustion device and pass to a gas/solid separator as described with regard to FIG. 1 above. The gaseous effluent may be further treated to remove any organic or other components by means known in the art such as oxidizers, scrubbers, or baghouses. The gaseous effluent then eventually passes into the atmosphere through a stack.

The Injection Subsystem

In accordance with the invention, there is provided an injection subsystem comprising an injector at a first location within the gaseous effluent downstream from any means for removing organic compounds from the gaseous effluent. The injector is disposed to inject at least one known organic compound into the gaseous effluent at a known rate.

Figure 2:
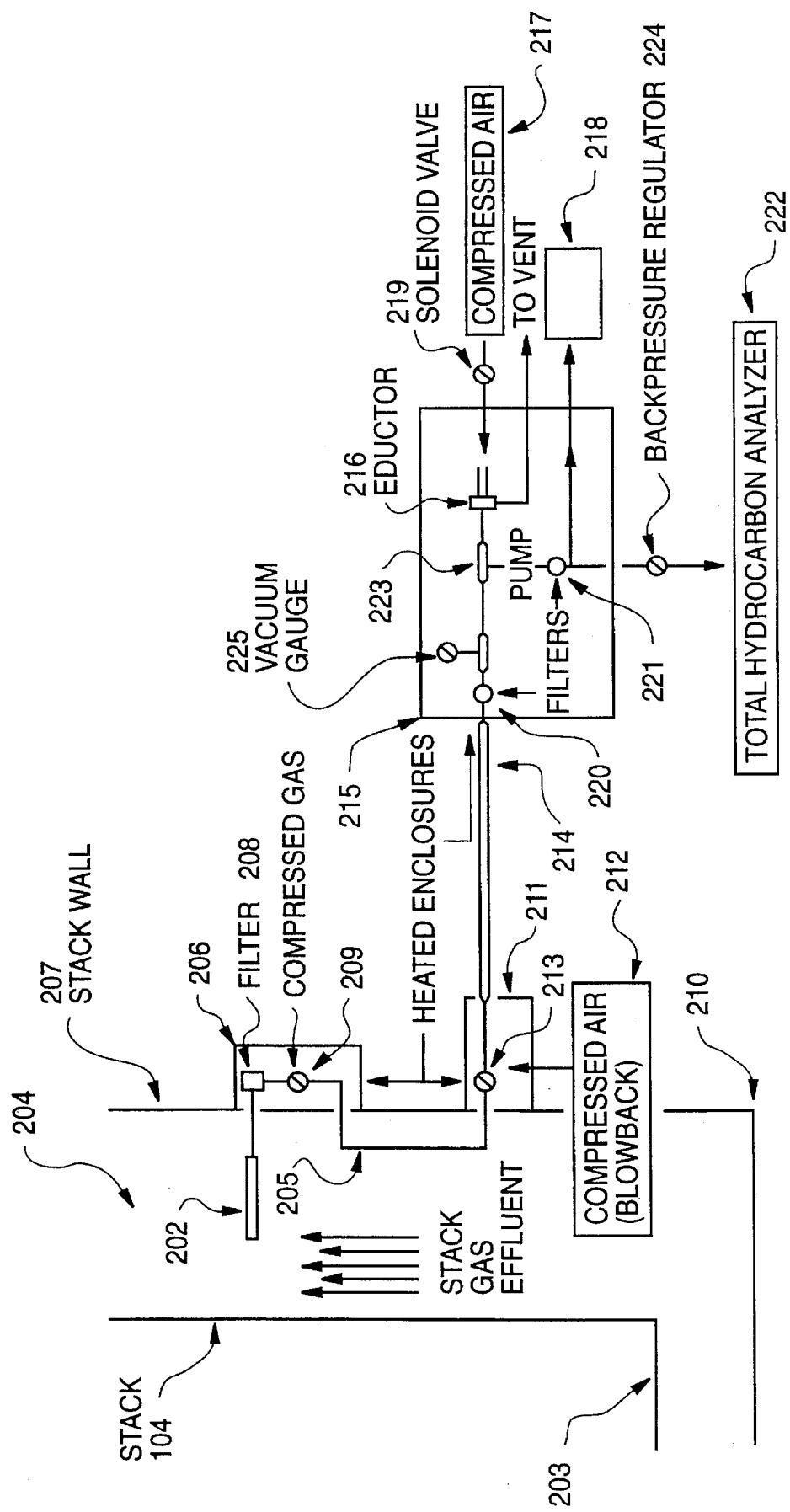
FIG. 2 is a schematic drawing of a preferred system for measuring $W_{out}$.

As embodied here and shown in FIGS. 1 and 2, the injector (105) is disposed upstream from the sampler (106).

The injector (105) can be a piece of rigid tubing extending into the effluent stream, and preferably is stainless steel tubing. Preferably, the injector is positioned after the bag houses and injects the organic compound into the intake of the induced draft fan, upstream from the stack (104). Injection of the organic compound into the induced draft fan permits homogenous mixing of the organic compound throughout the gaseous effluent.

Figure 4:
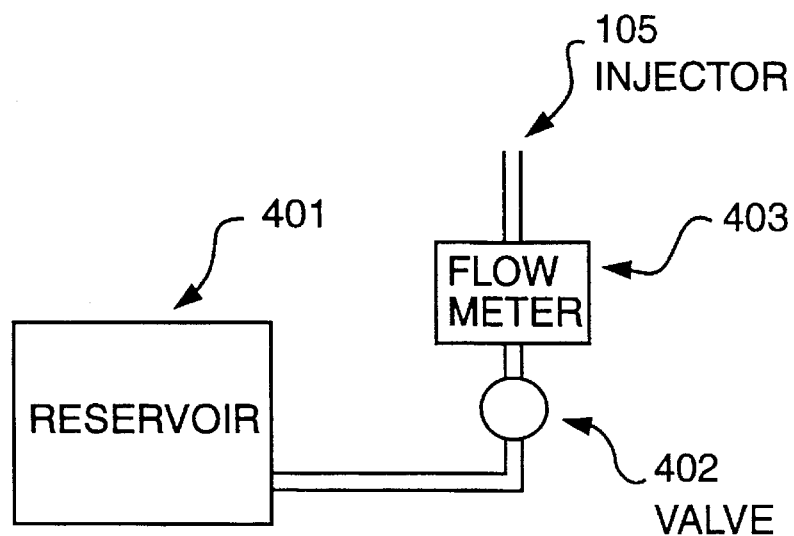
FIG. 4 is a schematic drawing of a preferred injection subsystem.

A preferred embodiment of the injector subsystem is shown in FIG. 4. The injector (105) is in flow communication with a pressurizable reservoir (401) capable of receiving the organic compound to be injected into the gaseous effluent. A preferred reservoir is a stainless steel cylinder capable of being filled with liquid or gaseous organic compounds for injection into the gaseous effluent. A one gallon capacity for this reservoir has proved to be sufficient.

Alternatively, to eliminate the pressurization, a pump (not shown) can be used to the deliver the organic compound from the reservoir (401) to the injector (105). Use of a computer controlled peristaltic pump for a completely automated injection subsystem is preferred.

A shut off valve (402), preferably a needle valve, can be installed at the output of the reservoir. A flow meter (403) is in flow communication with the reservoir and the injector (105), permitting the rate of organic material being injected into the gaseous effluent to be determined. Teflon™ tubing is preferably used to connect the reservoir and the flow meter. Small diameter tubing is preferably used to connect the flow meter to the injector. The small diameter tubing, preferably 0.003 in ID stainless steel tubing, drops the flow down for added control of the flow rate. An additional valve, preferably a needle valve, can be installed at the output of the flow meter to further aid in setting the flow rate. The preferred flow meter for use in the injection subsystem is the same as that discussed above for the introduction and combustion subsystem.

When high DRE values are required to be shown for a thermal combustion device and the device is operating at or above the desired DRE, the concentration of the organic compound or POHC in the gaseous effluent may be below the detection limit of the detector. Therefore, according to this invention, an amount of the organic compound of interest, sufficient to be detected by the detector, is injected into the gaseous effluent at or slightly below the level of $W_{out}$ for a given DRE. By detecting the presence of the organic compound in the gaseous effluent at that level insures that the detector is working properly and is capable of detecting the presence of the organic compound in the gaseous effluent at the specified DRE. Thus, if the organic compound is not detected in routine monitoring of the gaseous effluent, this injection procedure demonstrates that the detector would have detected the organic compound if present and that the thermal combustion device must be operating at or above the desired DRE.

The function of the injection subsystem, therefore, is to inject the known organic compound into the gaseous effluent at a known rate such that it can be detected at a rate less than or equal to a calculated $W_{out}$. Knowing the amount and rate $W_{in}$ of an organic compound introduced into the thermal combustion device and a desired DRE, an expected $W_{out}$ can be calculated. The desired DRE can be one mandated by environmental regulations or one set by the preferred operating parameters of the thermal combustion device.

One of ordinary skill would understand that the calculated expected value for $W_{out}$ can be converted to an expected concentration of a given organic compound in the gaseous effluent using unit conversions. Preferably, the concentration is converted to units of parts per billion (ppb). To convert the expected $W_{out}$ to concentration, one must know the stack flow in dry standard cubic feet per minute (dscfm) and the molecular weight of the organic compound of interest. The stack flow can be measured by means known in the art such as a pitot tube and converted to dscfm by taking into account the amount of water in the gaseous effluent. The amount of water can be determined using a mass spectrometer-based continuous emission monitoring system (CEMS), discussed below.

Injecting an amount of the known organic compound into the effluent ensures that there will be some concentration of the organic compound in the effluent stream to be detected. As discussed above, setting this concentration to be less than or equal to $W_{out}$ calculated for a desired DRE, it can be reliably shown that the thermal combustion device is operating at the desired level, even if no organic compound is detected in the gaseous effluent during normal operation or from the known organic compound introduced into the device to establish $W_{in}$.

The concentration of organic compound injected meets, or preferably exceeds, the detection limit of the detector in the detecting subsystem. In order to reliably read the concentrations of the organic compound in the gaseous effluent and emitted from the stack, it is most preferable for the concentration to be approximately five times the detection limit of the detector, i.e. approximately 50 ppb for a mass spectrometer. Particular concentrations may vary depending on the feed rate $W_{in}$, the stack flow rate and the thermal combustion devices actual DRE.

To achieve the appropriate concentration in the gaseous effluent, the organic compound can be injected as dilute solution in an appropriate organic solvent. Preferred dilutions range from 1:10 to 1:20, compound:solvent. The solvent is chosen based upon the solubility of the organic compound. Mixtures of two or more solutes or solvents may be used.

Sample Extraction Subsystem

In accordance with the invention there is provided a sample extraction subsystem comprising a sampler at a second location within the gaseous effluent downstream from the injector. The sampler is disposed to extract samples of the gaseous effluent. The sample extraction subsystem preferably includes at least one heated transfer line in flow communication with the sampler. The sample extraction subsystem allows for continuous sampling of the gaseous effluent and, therefore, continuous monitoring of the various components of the gaseous effluent. The sample extraction system may also sample the gaseous effluent intermittently. The entire extraction subsystem is heated to provide representative samples of the gaseous effluent without loss of components due to condensation and/or adsorption on system surfaces.

As here embodied and depicted in FIGS. 1 and 2, a sampler (106) is installed inside the exhaust stack (104) midway between the input conduit (203) and the exhaust end of the stack (204). In this embodiment, the sampler (106) is preferably a sample probe consisting of a stainless steel tube (202) having holes drilled in it to allow the gaseous effluent to be sampled. Preferably, the sampler is placed approximately 8 stack diameters downstream from the input conduits of the fans driving the effluent through the exhaust stack, and 8 stack diameters upstream from the effluent exhaust at the end of the stack.

A transfer line (205) then runs through the exhaust stack (104) and within, and essentially parallel to, the gaseous effluent stream to allow the heat of the exhaust stack to maintain the desired sample temperature. Alternatively, a heated exterior transfer line running outside the stack (not shown), external to the gaseous effluent, can be employed. A transfer line running within the gaseous effluent is preferred because it eliminates the need for heating and maintaining a long exterior transfer line.

As here embodied the transfer line runs from the sampler to a heated maintenance enclosure (206) mounted on the exhaust stack wall (206) which facilitates maintenance of the sampler (106) and provides a filter (208) and a connection (209) for the introduction of compressed gas for blowback or standard gases for calibration and testing.

At or near the base of the stack (210), the heated transfer line (205) enters a second heated enclosure (211). A source of compressed air (212) may be connected, preferably via a valve (213) to the transfer line (205) to blow back the system periodically to avoid transfer line and filter blockage. The second heated enclosure (211) may also house a series of filters (not shown) to remove large and small particulates. Preferable filters are ceramic or glass microfiber filters. Most preferable for the removal of small particulates (having sizes less than about 5 microns to about 0.1 micron) are the microfiber filters. The exhaust gas sample then passes through a second heated transfer line (214) to the analyzing subsystem. The second heated transfer line (214) is preferably insulated and electrically heated.

The purpose of the sample extraction subsystem is to provide compositionally representative samples to the analyzing subsystem.

The Analyzing Subsystem

In accordance with the invention, there is provided an analyzing subsystem in flow communication with the transfer line. The analyzing system is capable of detecting at least one organic compound within the gaseous effluent.

As embodied here and shown in FIG. 2, the analyzing subsystem is preferably heated to preserve the composition of the sample. The analyzing subsystem comprises a pump (216), preferably an eductor connected to a source of compressed air (217), for moving at least 10 (preferably about 15 and more preferably 20) liters per minute of the exhaust gas sample from the stack (104) to the heated enclosure (215) upstream from a detector (218). The detector is preferably a mass spectrometer used to detect the presence of organic compounds in the sampled effluent.

The sample extraction subsystem, described above, and the analyzing subsystem are preferably equipped with low temperature (preferably <150° C.) cutoffs for all heated enclosures (206, 211 and 215) and the heated transfer line (214) which close a solenoid valve (219) at the compressed air source (217) for the eductor (216). This insures that the sampled gaseous effluent does not flow in the event of a heater failure.

The analyzing subsystem may also contain a series of filters (shown in FIG. 2 as 220–221) to further remove large or small particulate material from the sampled effluent. Preferred filters are ceramic filters or microfiber filters. In the preferred embodiment, only particles smaller than 0.1 micron may pass the final filter.

In the preferred embodiment shown in FIG. 2, the exhaust gas sample, after filtration, is split and directed through a filter (221) to a total hydrocarbon analyzer (222). A second pump (223), preferably a diaphragm pump equipped with a back pressure regulator (224) at the outlet side of the pump, insures that an appropriate flow of sample is delivered to the detector (218), in this embodiment, a mass spectrometer. To measure pressure within the system, a vacuum gauge (225) can be placed upstream from the pump (223).

The filtered exhaust gas sample may also be connected to the mass spectrometer through a computer-controlled rotary valve (not shown). The rotary valve may also have connections (not shown) to facilitate the injection of mass spectrometer calibration gases.

Any variety of analytical device and/or technique capable of detecting the presence of organic compounds in a gaseous sample can be used as the detector in the present invention. Preferably, the detector is a mass spectrometer.

The mass spectrometer preferably used in the invention is a process mass spectrometer which continuously introduces the sampled gaseous effluent stream directly into the analyzer and monitors specific ion intensities for each component in the stream. A preferable mass spectrometer is a Questor Process Analyzer manufactured by Extrel Corporation of Pittsburgh, Pa., U.S.A.

In such a device, when the sample enters the mass spectrometer's vacuum chamber, it enters a region referred to as an electron impact ion volume. Some percentage of the sample molecules collide with electrons thereby producing positively charged molecular ions and fragment ions. The ions thus formed are electrically removed from the ion region using a series of lenses and are "shot" into the quadrupole mass filter which separates the ions according to their mass-to-charge ratio. A mass spectrum, a plot of ion intensity versus mass-to-charge ratio, for every component is unique. In process mass spectrometry, a single ion is chosen for each component to be analyzed. In situations where the ion intensity is the result of several components in the stream, the component of interest is resolved mathematically by subtraction of the interfering components' ion intensities.

An appropriate ion for the organic compound to be monitored can be easily selected by one skilled in the art and the mass spectrometer's data system to create an "analysis method". The concentration within the sampled effluent of the organic compound of interest is determined by its ion intensity. The concentration is determined by comparing the unit ion intensity measured with the unit ion intensity of the same compound from a calibration standard solution of known concentration. The mass spectrometer can also be set up to automatically calibrate itself using certified standard blends which can be connected to the rotary valve. The calibration routine takes approximately ten minutes to complete and can be performed before or after sampling the gaseous effluent.

In the present invention, the sampling and analyzing subsystems are also preferably employed as a continuous emissions monitoring system (CEMS). A mass spectrometer based CEMS according to this embodiment can continuously monitor, not only a known organic compound used to determine the thermal combustion device's DRE but also other by-products or pollutants, such as $SO_2$, nitrogen oxides (as NO), HCl, $Cl_2$, $N_2$, $O_2$, $CO_2$ and Ar. The mass spectrometer can also used to determine the amount of water in the gaseous effluent to provide the necessary data to determine the stack flow in dscfm.

An analysis of such components within the gaseous effluent can be completed approximately every ten seconds with the data reported locally and sent to a control computer. This real time analysis allows the components of the gaseous effluent to be monitored only a short time after the gaseous effluent is generated in the thermal combustion device. Process parameter adjustment may then be accomplished under actual working conditions.

The system for assessing the destruction and removal efficiency of a thermal combustion device according to the present invention may be a fixed part of the device's architecture or can be configured as a removable system. A removable system according to the present invention needs only access for the various subsystems to the appropriate part of the device to accomplish their respective functions. The needed access is preferably by penetration of existing openings in the device's architecture. With regard to the sampling subsystem, the removable embodiment of the invention can comprise a sampler conduit, having an inlet, removably placed within the gaseous effluent stream to extract samples of the gaseous effluent. The sampler conduit is in flow communication with the heated transfer line as described for the sampler above. In a particularly preferred embodiment, the sampler conduit is lowered into the gaseous effluent of a stack or passed through an existing opening in the stack wall and the heated transfer line runs outside the stack to the analyzing subsystem. The removable system has the advantage that it may be used at more than one thermal combustion device.

The present invention also relates to an indirect method of assessing the destruction and removal efficiency of a thermal combustion device combusting hazardous waste and having a gaseous effluent. The method, rather than calculating the DRE directly, provides a straight forward means for assessing whether or not the thermal combustion device is operating at a desired DRE. The method uses the following formula:

$$DRE=100\times(W_{in}-W_{out})/W_{in}$$

where:

$W_{in}$=mass feed rate of an organic compound into the device, and $W_{out}$=the mass emission rate of the organic compound in the gaseous effluent. The method described here is particularly suitable for the thermal combustion devices using material containing hazardous organic compounds as fuels and feedstocks and for thermal combustion devices which are used to destroy hazardous wastes containing organics.

The method permits real time analysis of the gaseous effluent and the device's DRE; that is, under actual working conditions and during actual operation of the device with only minimal time delay. Real time analysis can allow for process parameter adjustment with a corresponding change in the device operation to improve or maintain the device's DRE.

According to the method, at least one organic compound is fed into the thermal combustion device at a known rate to provide $W_{in}$. The method of this invention can be used to assess the DRE for more than one organic compound in the gaseous effluent. The organic compound can be fed into the device during normal operation with material normally combusted in the operation of the device.

The organic compound fed into the device is combusted to form a gaseous effluent. The organic compound is preferably combusted with other material normally combusted in the operation of the thermal combustion device.

In a preferred embodiment, the gaseous effluent is sampled and the concentration of the known organic compound in the gaseous effluent measured. The preferred sampling step is performed during the combusting step. If the organic compound is detected in the gaseous effluent, the thermal combustion device's DRE can be calculated directly. To calculate the DRE, the concentration of the organic compound in the gaseous effluent is converted to the mass emission rate $W_{out}$ and the DRE calculated using the known mass feed rate $W_{in}$ according to the equation above.

If the organic compound is not detected in the gaseous effluent, the thermal combustion device's DRE can be demonstrated using an indirect method of assessing DRE according to the present invention.

Before, after or concurrently with the combustion step, the preferred sampling or the preferred measuring step, an expected $W_{out}$ can be calculated for each organic compound of interest. The expected $W_{out}$ is calculated from the known rate $W_{in}$ of a known organic compound (or known organic compounds) fed into the device and by designating a desired DRE. The calculated $W_{out}$ can then be converted to an expected concentration for the organic compound of interest in the gaseous effluent as discussed above.

The desired DRE used to calculate an expected $W_{out}$ can be one mandated by environmental regulations for a given organic compound or one based on preferred operating parameters for the thermal combustion device. Preferably the DRE may be equal to or slightly less than 99.99 percent, i.e. 99.988 percent.

An amount of the organic compound to be detected is then injected into the gaseous effluent at a known rate less than or equal to $W_{out}$. The amount of organic compound injected must be sufficient to permit detection by the detector. As discussed above, the organic compound is injected into the gaseous effluent at a location downstream from any means for combustion or otherwise removing the organic compound from the gaseous effluent. Preferably, the time during which the organic compound is injected into the gaseous effluent is finite in length.

During the injection step, the gaseous effluent is sampled at a location downstream from the location of the injection and the concentration of the organic compound in the sampled effluent is measured. Preferably, a single sampler is used for both sampling steps. Most preferably, the gaseous effluent is continuously sampled and its composition monitored using a mass spectrometer-based CEMS. Prior to measuring the concentration of the organic compound in the sampled effluent, the sampled effluent is preferably hot filtered to remove any particulate matter.

By comparing the concentration of the organic compound in the sampled effluent during the injection step with the expected concentration based on the calculated $W_{out}$, one can readily determine whether or not the thermal combustion device is operating at the desired DRE. Alternatively, the concentration of the organic compound in the gaseous effluent can be converted to the rate $W_{out}$, the DRE calculated and compared with the desired DRE. The latter method of determining the DRE of a thermal combustion device may be preferable when demonstrating DRE values less than a desired value and when the method contains the steps of sampling and measuring the concentration of the known organic compound in the gaseous effluent prior to the injection step.

The gaseous effluent itself may be continuously monitored using the sample extraction and analyzing subsystems described above during and/or prior to any step of a method according this invention. This continuous monitoring can be for the organic compound to be introduced according to the method of this invention or for other components of the gaseous effluent.

Example 1 below demonstrates a calculation of DRE using the method of this invention. FIG. 3 shows a schematic of the introduction system used in this Example 1. A 500 gallon (1,900 L) tank is filled with $CCl_4$. A variable rate diagram pump with a maximum pumping capacity of 2 gpm (7.6 L/min) is located at the outlet of the tank. The actual $CCl_4$ flow is measured using a differential pressure flow meter. Downstream from the flow meter, the $CCl_4$ passes through approximately ten feet (3 m) of ½" (1.77 cm) OD tubing before introduction into oil that is combusted in the system being evaluated. It should be noted that, while the methods described above are entirely general, recent environmental regulation of $CCl_4$ no longer permits it to be used as the organic compound or POHC of choice for a DRE determination. Reliable determinations using the methods described here have been made using carbon tetrachloride and chlorobenzene as the organic compound or POHC.

FIG. 4 shows a schematic of the injection system used to introduce a small amount of $CCl_4$ downstream from the baghouse filters. A one gallon (3.8 L) stainless steel cylinder is filled with a solution of $CCl_4$ in methylene chloride, $CH_2Cl_2$. Compressed $N_2$, at 40 psi (275 kPa gauge) provides positive pressure over the mixture. A shut-off valve is installed at the output of the cylinder. Teflon™ tubing is used to connect the cylinder output to a flow meter. A second needle valve is installed at the output of the flow meter to aid in setting flow rate. The sample is injected into the intake of the induced draft fan using approximately 35 feet (10.6 m) of ¹⁄₁₆" (0.16 mm) OD stainless steel tubing.

EXAMPLE 1

The present invention was compared to a conventional method of determining a DRE. The value of the DRE directly measured using the trial burn method was, for three runs, 99.998%, 99.999% and 99.999%, for an average DRE of 99.999%. With a DRE of 99.999%, to directly measure $W_{out}$ with a mass spectrometer based CEMS at 50 ppb a feed rate of $CCl_4$ of approximately 6,2000 lb/hour (2,828 kg/hour) would be required. At a feed rate of 6,200 lb/hour (13,640 kg/hour) of $CCl_4$, 5,870 lb/hr (2,668 kg/hour) or approximately 20,100 ppm HCl would be produced and would be a significant load for a conventional scrubbing system. In addition, the $CCl_4$ cost would be approximately $4,340.00/hour. Thus, to directly determine a DRE in this manner, both the HCl production and $CCl_4$ cost are considered intolerably high.

Therefore, it was decided to indirectly demonstrate a 99.99% DRE rather than make a direct determination. The steps to demonstrate the DRE by indirect measurement according to the present invention are:

1) Set $W_{in}$, the feed rate of $CCl_4$ to the thermal combustion device, at approximately 700 lb/hr (318 kg/hour).
2) Set the mass spectrometer detector gain for a detection limit of 10 ppb for $CCl_4$, with good repeatability at 50 ppb.

With a DRE of 99.99% at a typical stack flow, the POHC emitted from the stack $W_{out}$ will be approximately 0.07 lb/hr (0.03 kg/hour) or 57 ppb $CCl_4$, a concentration which is within regulatory limits can be reliably measured by the mass spectrometer. If the DRE is greater than 99.99%, for example 99.997%, $W_{out}$ will be only 0.021 lb/hr (0.01 kg/hour) or 17 ppb. At this low level, the $CCl_4$ concentration may not be accurately or reliably read by the CEMS.

3) To confirm that at least 0.07 lb/hr $CCl_4$ would have been measured by the CEMS, had it been present, 0.07 lb/hr $CCl_4$ are introduced to the system where it will not be oxidized or removed, e.g., in the stack. The concentration of $CCl_4$ in the stack gas downstream is measured at levels at or below what can be accurately and reliably measured by the CEMS.

EXAMPLE 2

Detection limit, linearity, accuracy and repeatability tests were conducted to confirm the mass spectrometer's capability to perform the DRE demonstration. The CEMS was equipped with a dual detector. For the DRE work, an electron multiplier detector, with a detection limit of approximately 10 ppb, was used.

Linearity and accuracy tests

The mass spectrometer was calibrated using 650 ppb $CCl_4$ in compressed $N_2$. As depicted in FIG. 4 an injection reservoir (401) contained a 1:20 dilution of $CCl_4:CH_2Cl_2$. The flow meter, calibrated using this solution, gave a useful flow range of 1.3 to 21.3 ml/min. To measure instrument linearity, the $CCl_4$ solution was introduced at the induced draft fan at various flow rates and the concentration emitted from the stack was measured by the CEMS. The expected concentration of an organic compound emitted from the stack when injected at a known flow can be calculated since the stack flow is also continuously monitored.

The expected concentration to be emitted from the stack was calculated for each rate of flow through the injection system. The stack flow was measured using a pitot tube with an estimated accuracy of ±10%.

Figure 5:
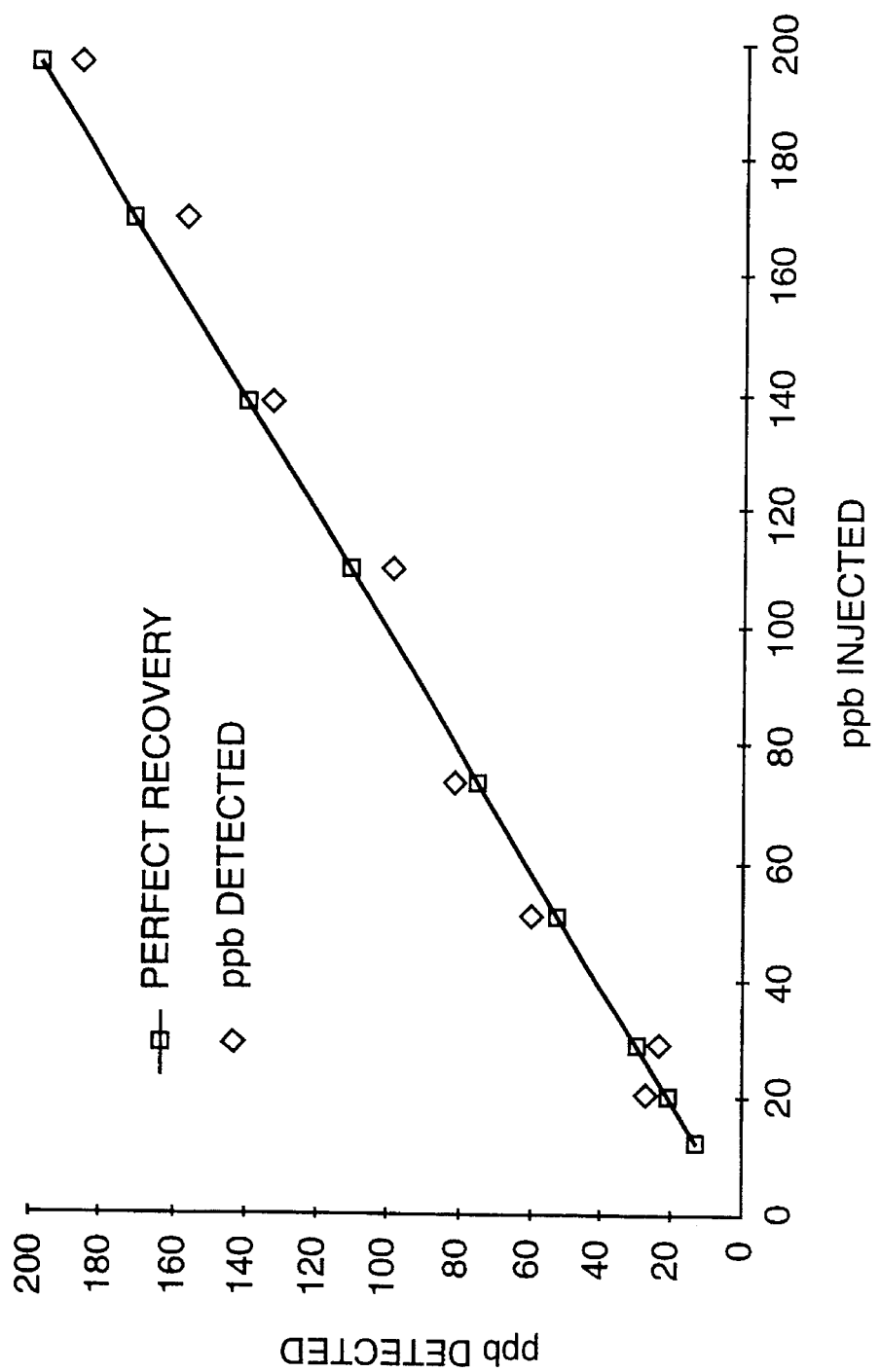
FIG. 5 is a plot showing the linearity and accuracy of a preferred system for determining the destruction and removal efficiency of a thermal combustion device.

The $CCl_4$ was injected over an expected concentration range of 12 ppb to 196 ppb. Each reading was an average of five one minute samples. FIG. 5 is a plot of the concentration of $CCl_4$ detected by the CEMS versus the expected emitted concentration. The plot shows excellent linearity over the concentration range tested.

Figure 6:
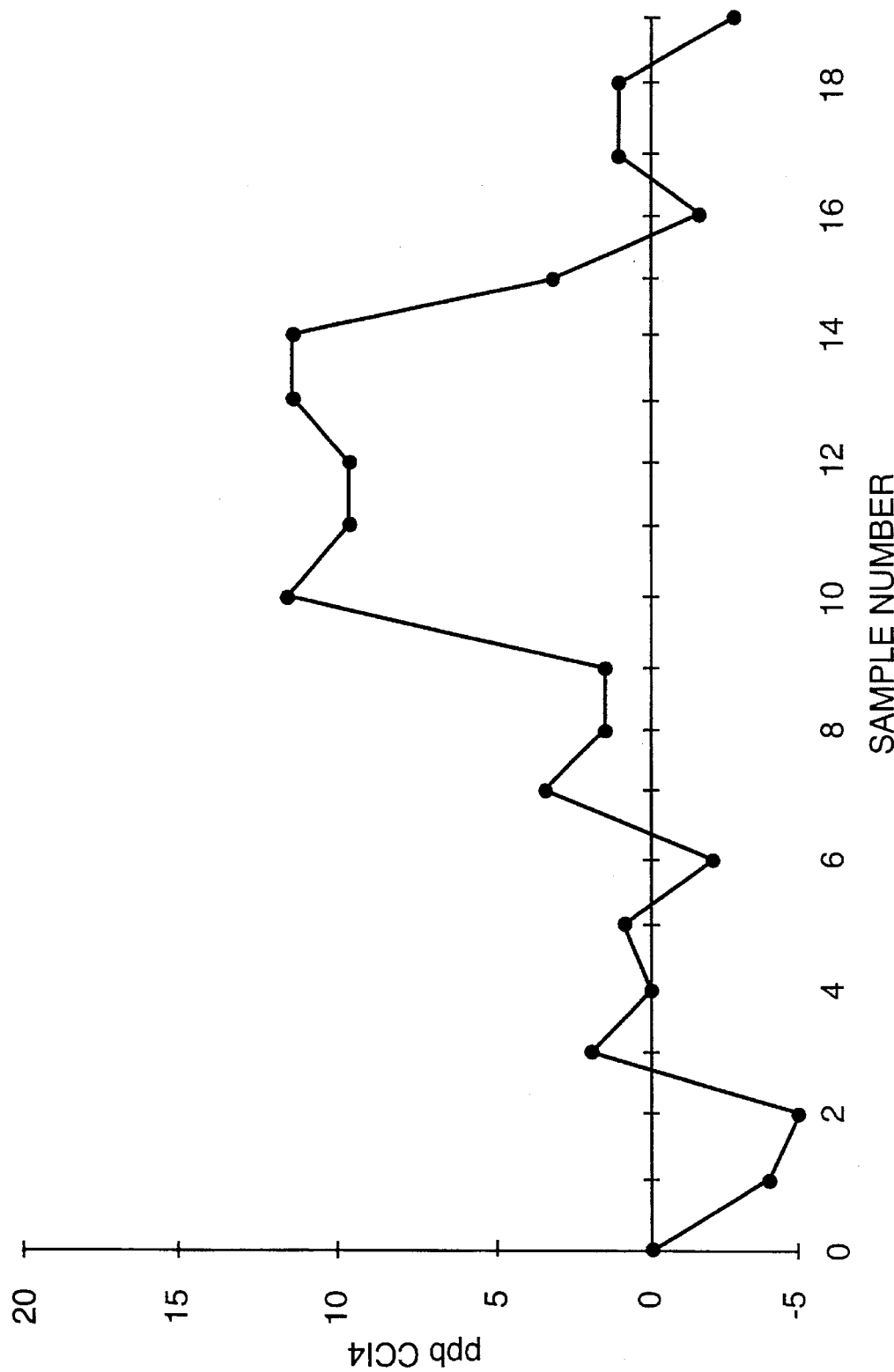
FIG. 6 is a plot of the detection limit for a mass spectrometer based system for determining destruction and removal efficiency.

Detection limit tests $CCl_4$ was injected in a similar manner to determine the CEMS detection limit. FIG. 6 is a plot of ppb $CCl_4$ detected by the CEMS versus sample number. Each point plotted is an average of six readings by the mass spectrometer. The points on the graph with sample numbers 0–9 and 16–19 indicate periods when the injection system was turned off in order to obtain CEMS noise. Sample numbers 10–14 show the CEMS readings, in ppb, when 12 ppb $CCl_4$ was introduced via the injection system. Typically, an instrument detection limit is defined as the point where the signal-to-noise ratio (S/N) is equal to 2/1, where noise is equal to one half the band width. The noise is approximately 4 ppb which would give a calculated S/N of 8 ppb. This calculation is confirmed by the data as the introduction of 12 ppb is readily detected with a relative standard deviation for the five readings of 9.1%.

The CEMS accuracy and precision for the tests described above are given in Table 1. At 60 ppb, the approximate concentration that will correspond to 99.99% DRE, the reliability of the test should be ±10% or 5 ppb. At a feed rate of 700 lb/hr and a typical stack flow of 52,000 dry standard cubic feet/minute (dscfm), a DRE change of 0.001% will change $W_{out}$ by 6 ppb. Given a reliability of ±5 ppb, a DRE change of 0.002% may be required in order to be detected by the CEMS. In other words, a DRE drop from 99.990% to 99.988%, which corresponds to a $W_{out}$ change from 57 ppb to 68 ppb, should be detected by the CEMS.

TABLE 1

| | CEMS Accuracy and Precision | | | | | | | |
|---|---|---|---|---|---|---|---|---|
| ppb | ppb | | | | Repeatability | | | Accuracy |
| Injected | Detected | | | | | Mean | Std. Dev | % RSD | % Error |
| 12 | 13, | 11, | 11, | 13, | 13 | 12 | 1.1 | 9.1 | 0.0 |
| 20 | 21, | 20, | 22, | 25, | 26 | 23 | 2.6 | 11.0 | 15.0 |
| 29 | 25, | 27, | 29, | 26, | 25 | 26 | 1.7 | 7.4 | 10.0 |
| 51 | 59, | 55, | 53, | 55, | 57 | 56 | 2.3 | 4.1 | 9.8 |
| 74 | 85, | 84, | 86, | 81, | 70 | 81 | 6.5 | 5.0 | 9.4 |
| 110 | 98, | 100, | 97, | 103, | 97 | 99 | 2.5 | 2.5 | 10.0 |
| 138 | 139, | 129, | 119, | 135, | 138 | 132 | 8.2 | 6.2 | 2.9 |
| 170 | 156, | 156, | 154, | 158, | 154 | 156 | 1.7 | 0.1 | 8.2 |
| 196 | 174, | 188, | 178, | 193, | 195 | 184 | 7.6 | 4.3 | 6.1 |

$$\% \text{RSD} = \frac{100 \, (\text{Std Dev.})}{\text{Mean}}$$

$$\% \text{Error} = \frac{(\text{ppb injected} - \text{ppb Detected})}{\text{ppb injected}} \times 100$$

The present invention has been disclosed in terms of various preferred embodiments, however, the scope of the invention is not limited to those embodiments. The scope of the invention is determined solely by the appended claims and their equivalents.

What is claimed is:

1. A method of assessing the destruction and removal efficiency (DRE) of a thermal combustion device having a gaseous effluent according to the formula $$DRE = 100 \times (W_{in} - W_{out})/W_{in}$$

where:

$W_{in}$ = mass feed rate of an organic compound into the device, and $W_{out}$ = the mass emission rate of the organic compound in the gaseous effluent;

said method comprising the steps of:

feeding at least one known organic compound into said device at a known rate to provide $W_{in}$;

combusting said organic compound to form a gaseous effluent;

sampling said gaseous effluent at a first location;

measuring with a detector the concentration of said organic compound in the sampled effluent;

calculating an expected $W_{out}$ for a desired DRE based on $W_{in}$;

assessing the DRE by comparing said expected $W_{out}$ to said measured concentration of sampled effluent, or, by converting said measured concentration to a rate value, calculating the DRE based on the rate value, and comparing the calculated DRE to said desired DRE;

injecting an amount of said organic compound into said gaseous effluent at a known rate less than or equal to the expected $W_{out}$ and sufficient to be detected, said organic compound being injected at a second location upstream from said first location and downstream from any means for removing said organic compound from said gaseous effluent;

sampling said gaseous effluent a second time at said first location; and measuring the concentration of said organic compound in the sampled effluent in real time to ensure the detector is capable of detecting the presence of the organic compound at the desired DRE.

2. The method of claim 1, further comprising hot filtering said sampled effluent prior to each of said measuring steps.

3. The method of claim 1, wherein the concentration of said organic compound in the sampled effluent is measured by mass spectrometry.

4. The method of claim 1, wherein said gaseous effluent is continuously sampled and the constituents of said gaseous effluent monitored by mass spectrometry.

5. The method of claim 1, wherein said organic compound is a hazardous organic compound.

6. The method of claim 1, prior to each of said measuring steps, further comprising the steps of transporting said sampled effluent in a first heated transfer line;

hot filtering said sampled effluent;

transferring said sampled effluent through a second heated transfer line to a heated analyzing system; and maintaining the flow rate of said sampled effluent of at least 10 liters per minute, and said sampled effluent at a temperature no less than about 190° C. in said system.

7. The method of claim 6 including the step of heating said first heated transfer line within said gaseous effluent to heat said sampled effluent to the desired temperature.

8. The method of claim 6 wherein said hot filtering step comprises filtration through a series of filters to remove small and large particulates.

9. The method of claim 8 further comprising a second filtration step after said transferring step wherein said sampled effluent is passed through a second series of filters located within said analyzing system to remove small and large particulates.

10. The method of claim 9, wherein the concentration of at least one organic compound in the sampled effluent is measured by mass spectrometry.

11. The method of claim 1, wherein said method is conducted in real time.

12. The method of claim 11, wherein said organic compound is a hazardous organic compound.

13. The method of claim 1, wherein the DRE used to calculate the expected $W_{out}$ is 99.988%.

14. A system for assessing the destruction and removal efficiency of a thermal combustion device having a gaseous effluent, said system comprising:

means for introducing at least one known organic compound into a thermal combustion device, means for combusting said organic compound, an injector at a first location within said gaseous effluent downstream from any means for removing organic compounds from said gaseous effluent, said injector being disposed to inject an amount sufficient for detection of at least one organic compound at a known rate into said gaseous effluent;

a sampler at a second location within said gaseous effluent downstream from said injector, said sampler being disposed to extract samples of said gaseous effluent;

at least one heated transfer line in flow communication with said sampler;

an analyzing system in flow communication with said transfer line, said analyzing system being capable of measuring the concentration of said organic compound within said gaseous effluent.

15. The system of claim 14, wherein said introduction means comprises a reservoir capable of receiving said organic compound;

a control valve in flow communication with said reservoir;

a flow meter in flow communication with said control valve; and a conduit in flow communication with said flow meter and disposed to introduce said organic compound into said device.

16. The system of claim 15, further comprising, prior to said heated transfer line, at least one heated filter in flow communication with said sampler.

17. The system of claim 16, wherein said analyzing system includes a mass spectrometer.

18. The system of claim 17 wherein said system includes a heated enclosure between said sampler and said heated filtering means, said enclosure including means for providing access to said sampler.

19. The system of claim 17, wherein said heated transfer line runs within, and essentially parallel to, said gaseous effluent.

20. The system of claim 17, wherein said heated transfer line is external to said gaseous effluent.

21. The system of claim 14, wherein said heated transfer line runs within, and essentially parallel to, said gaseous effluent.

22. The system of claim 14, wherein said heated transfer line is external to said gaseous effluent.

23. The system of claim 14, wherein said system is a removable system.

24. A method of assessing the destruction and removal efficiency (DRE) of a thermal combustion device having a gaseous effluent according to the formula $$DRE=100\times(W_{in}-W_{out})/W_{in}$$

where:

$W_{in}$=mass feed rate of an organic compound into the device, and $W_{out}$=the mass emission rate of the organic compound in the gaseous effluent;

said method comprising the steps of:

feeding at least one known organic compound into said device at a known rate to provide $W_{in}$;

calculating an expected $W_{out}$ for a desired DRE based on $W_{in}$;

combusting said organic compound to form a gaseous effluent;

injecting an amount of said organic compound into said gaseous effluent at a known rate less than or equal to the expected $W_{out}$ and sufficient to be detected, said organic compound being injected at a first location downstream from any means for removing said organic compound from said gaseous effluent;

sampling said gaseous effluent at a location downstream from said first location; and measuring with a detector the concentration of said organic compound in the sampled effluent in real time;

assessing the DRE by comparing the expected $W_{out}$ to the concentration of the organic compound in the sampled effluent, or, by converting said measured concentration to a rate value, calculating the DRE based on the rate value, and comparing the calculated DRE to said desired DRE;

wherein said injecting and measuring steps ensure the detector is capable of detecting the presence of the organic compound at the desired DRE.

* * * * *